US008187317B2

(12) United States Patent
Leprince et al.

(10) Patent No.: US 8,187,317 B2
(45) Date of Patent: May 29, 2012

(54) ENDOPROSTHESIS, AND METHOD FOR PRODUCING AN ENDOPROSTHESIS

(75) Inventors: Pascal Leprince, Rueil Malmaison (FR); Mourad Karouia, Bagneux (FR); Johan Mazeyrat, Antony (FR); Olivier Romain, Montgeron (FR); Pierre-Yves Lagree, Gentilly (FR); Patrick Garda, Thiais (FR); Hamid Kokabi, Villeneuve la Garenne (FR)

(73) Assignees: Universite Pierre et Marie Curie-Paris VI, Paris (FR); Centre National de la Recherche Scientifique (C.N.R.S.), Paris (FR); Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 12/439,724

(22) PCT Filed: Sep. 4, 2007

(86) PCT No.: PCT/FR2007/001431
§ 371 (c)(1),
(2), (4) Date: Dec. 9, 2009

(87) PCT Pub. No.: WO2008/029020
PCT Pub. Date: Mar. 13, 2008

(65) Prior Publication Data
US 2010/0094406 A1 Apr. 15, 2010

(30) Foreign Application Priority Data

Sep. 4, 2006 (FR) ...................................... 06 07733

(51) Int. Cl.
*A61F 2/06* (2006.01)
(52) U.S. Cl. ........................ 623/1.13; 623/1.34; 600/561
(58) Field of Classification Search ................. 623/1.13, 623/1.15, 1.34, 1.44; 600/561
See application file for complete search history.

(56) References Cited

U.S. PATENT DOCUMENTS
2003/0229388 A1  12/2003  Hayashi et al.

FOREIGN PATENT DOCUMENTS
| EP | 0 897 690 | 2/1999 |
| WO | 02/098296 | 12/2002 |
| WO | 03/047419 | 6/2003 |
| WO | 2004/105637 | 12/2004 |

OTHER PUBLICATIONS
International Search Report dated Mar. 25, 2008, from corresponding PCT application.

*Primary Examiner* — Bruce E Snow
(74) *Attorney, Agent, or Firm* — Young & Thompson

(57) ABSTRACT

The endoprosthesis is designed to be implanted in an aneurysm (12) of a patient, the aneurysm (12) resulting from deformation of a vessel wall, in particular the wall of an artery (14), the endoprosthesis including: a tubular envelope (22, 24) that extends in a direction (Y-Y'), and a plurality of pressure probes (26) fixed on the envelope (22, 24), each probe (26) including: a sensor (28) for measuring pressure, and elements (34, 36) for transmitting the pressure measurement to a monitoring apparatus located outside the patient. The elements (34, 36) for transmitting the pressure measurement from each probe (26) are designed to generate an electromagnetic pressure measurement transmission signal including at least one distinctive characteristic of the probe (26) of which these elements (34, 36) form part.

9 Claims, 3 Drawing Sheets

ENDOPROSTHESIS, AND METHOD FOR PRODUCING AN ENDOPROSTHESIS

BACKGROUND OF THE INVENTION

1. Field of the Invention

The present invention relates to a tubular endoprosthesis which is to be implanted in an aneurysm of a patient. The invention relates also to a method for producing a tubular endoprosthesis.

2. Description of the Related Art

A weakness in a wall of an artery of a human being can lead to the local dilatation of the artery and form an aneurysm. The aneurysm can endanger the patient's life because of the risk of internal bleeding (hemorrhage) resulting from a rupture of the arterial wall. Such a rupture is the result, for example, of the application of a blood pressure to the weakened wall of the artery.

Aneurysms are conventionally treated before a rupture occurs. Two surgical operations can be carried out:
1. A conventional operation or ablation of the aneurysm is carried out.
2. A mini-invasive endovascular operation via the femoral arteries is carried out. This operation consists in excluding the aneurysm from blood circulation by positioning an endoprosthesis in the region of the aneurysm. The endoprosthesis is intended to replace the artery in the region of the aneurysm.

Although the procedure of fitting the endoprosthesis is now well known, there is still a risk that leaks will occur, that is to say that the aneurysm will not be perfectly excluded, either immediately after the operation or several months later. Such leaks are called "type I or type II endoleaks" according to their origin (migration of the endoprosthesis due to inadequate anchoring, existence of blood circulation in the excluded aneurysmal sac due to subrenal collateral criteria, etc.).

Accordingly, it is essential to monitor the endoprosthesis and the aneurysm in order to detect endoleaks and, especially, prevent a risk of post-operative rupture. It would be advisable in this case to carry out the most appropriate operation.

Such monitoring can be carried out by medical imaging, such as magnetic resonance imaging, but this is restricting for the patient.

Another possibility, described in U.S. Pat. No. 6,159,156, is to place in the aneurysm an identical pressure probe from which measurements will be collected by means of a device outside the patient's body. This document also describes the fixing of a probe to the endoprosthesis so that the probe retains a fixed position in the aneurysm.

This document proposes determining a risk of rupture when an excessively high pressure or a pressure that has changed greatly relative to a preceding measurement is detected somewhere in the aneurysm.

Nevertheless, it has been found that this solution often leads to incorrect conclusions, especially false alarms. The method therefore lacks accuracy.

SUMMARY OF THE INVENTION

An object of the invention is to remedy this problem by improving the detection of a weakness in the aneurysmal wall.

Endoprosthesis for implantation in an aneurysm 12 of a patient, the aneurysm resulting from a deformation of a vessel wall, in particular an arterial wall 14, comprising:
 a tubular envelope 22, 24 which extends according to a direction Y-Y', and
 a plurality of pressure probes 26 fixed to the envelope 22, 24, each probe 26 comprising:
 a sensor 28 for carrying out a pressure measurement, and
 means 34, 36 for transmitting the pressure measurement to a monitoring device located outside the patient's body, the endoprosthesis being characterized in that the means 34, 36 for transmitting the pressure measurement of each probe 26 are suitable for generating an electromagnetic pressure measurement transmission signal containing at least one characteristic that is distinctive to the probe 26 of which the means 34, 36 form part.

The inventors have in fact found that in the excluded aneurysmal sac there is a blood clot, a "thrombus", which will locally modify the pressure distribution. Accordingly, the existence of a pressure of a certain value at a given location in the aneurysm can be entirely normal, even though at another location in the aneurysm it is elevated and may cause a rupture. The use of a threshold for detecting a risk of rupture is therefore unsuitable.

By virtue of the invention it is possible to obtain the development of the pressure measurement carried out for each probe because it is possible to differentiate between the measurements transmitted by each probe. Accordingly, when the pressure measured by a probe suddenly increases between two consecutive measurements, even when the measurements from the other probes have not varied, it is highly probable that the aneurysmal wall is weakened and that rupture is imminent.

An endoprosthesis characterized in that the distinctive characteristic is contained in the digital data sent in the transmission signal.

An endoprosthesis characterized in that:
 the sensor 28 is suitable for supplying an analogue electrical signal,
 the endoprosthesis 20 comprises a low noise amplifier 30 for amplifying the analogue signal before it is introduced into the means 34, 36 for transmitting the pressure measurement to the monitoring device.

An endoprosthesis characterized in that:
 the means 34, 36 for transmitting the pressure measurement are intended to generate a transmission signal which encodes digital data,
 the endoprosthesis 20 comprises an analogue/digital converter 32 for converting the analogue signal supplied by the sensor 28 and amplified.

An endoprosthesis characterized in that the probes 26 are distributed in one or more groups of probes 26A, 26B, the probes of each group 26A, 26B being fixed at regular intervals around the endoprosthesis 20 on the same section 27A, 27B of the endoprosthesis 20.

An endoprosthesis characterized in that the sensor 28 of each probe of the plurality is a directional sensor, its sensitivity being maximal for pressures exerted perpendicularly to its measurement surface.

An endoprosthesis characterized in that the deformation is a dilatation and the probes 26 are oriented towards the outside of the envelope 22, 24.

An endoprosthesis characterized in that the deformation is a retraction and the probes 26 are oriented towards the inside of the envelope 22, 24.

An endoprosthesis characterized in that the transmission signal has a carrier frequency within one of the free frequency bands defined in the ISM standard.

Method for producing an endoprosthesis 20 for implantation in an aneurysm 12 of a patient, the aneurysm resulting from a deformation of a vessel wall, in particular an arterial wall 14, comprising:

a tubular envelope 22, 24 which extends according to a direction Y-Y', and a plurality of pressure probes 26 fixed to the envelope 22, 24, each probe 26 comprising:

a sensor 28 for carrying out a pressure measurement, and means 34, 36 for transmitting the pressure measurement to a monitoring device located outside the patient's body, the means 34, 36 for transmitting the pressure measurement of each probe (26) being suitable for generating an electromagnetic pressure measurement transmission signal containing at least one characteristic that is distinctive to the probe 26 of which the means 34, 36 form part, the method being characterized in that it comprises the following steps:

producing the envelope 22, 24, fixing of the pressure probes 26 to the envelope 22, 24.

A method according to the invention can further have one or more of the following features:

in order to produce an endoprosthesis in which the sensor of each probe of the plurality is a directional sensor, its sensitivity being maximal for pressures exerted perpendicularly to its measurement surface, the method further being characterized by the following steps:

obtaining a visual representation of the aneurysm 12 of the patient by medical imagery, and producing an envelope 22, 24 of a shape adapted to that of the aneurysm 12, locating at least one local pressure maximum A, B exerted on the wall 14 of the aneurysm 12 of the patient by blood flows within the aneurysm 12, and fixing at least one of the pressure probes 26 to the envelope 22, 24, the probe 26 being oriented towards the outside of the envelope 22, 24 so that the probe 26 is oriented towards the local pressure maximum when the endoprosthesis 20 is implanted in the aneurysm 12.

A method characterized in that it comprises the following steps:

deriving a model of the aneurysm 12 from the visual representation, and locating by calculation the local pressure maximum or maxima A, B exerted on the wall 14 of the modelled aneurysm 12.

A method characterized in that the visual representation is a view from a scanner or MRI.

A method characterized in that, in order to fix the pressure probe 26 to the endoprosthesis 20, the method comprises the following steps:

choosing a configuration for fitting of the endoprosthesis 20 from the model of the aneurysm 12, such that the endoprosthesis 20 extends along a direction X-X' of flow of the blood flow, determining a zone 27A, 27B for the fixing of sensors 26 to the envelope 22, 24 of the endoprosthesis 20, such that the local maximum A, B is located perpendicularly to the fixing zone 27A, 27B relative to the envelope 22, 24, and fixing the pressure probe 26 to the fixing zone 27A, 27B, the probe 26 being oriented perpendicularly to the envelope 22, 24 towards the outside of the endoprosthesis 20.

A method characterized in that it comprises the following steps:

determining an at-risk portion A, B of the aneurysm 12, perpendicular to the direction of flow X-X' and forming the local maximum, determining along the direction Y-Y' of the envelope 22, 24 in the configuration for fitting of the endoprosthesis 20, a section 27A, 27B of the envelope 22, 24 delimited by the at-risk portion A, B the section forming the zone for fixing of the pressure probe 26.

A method characterized in that the at-risk portion A, B has a thickness corresponding to a dimension exhibited by the pressure probe 26 along the direction Y-Y' of the envelope 22, 24 when the probe 26 is fixed.

A method characterized in that it comprises the following step:

fixing a plurality of probes 26 to the fixing section 27A, 27B around the direction of the endoprosthesis Y-Y'.

Method according to claim 8, characterized in that the probes 26 are distributed around the direction Y-Y' of the envelope 22, 24 at regular intervals.

BRIEF DESCRIPTION OF THE DRAWING FIGURES

The invention will be better understood from reading the following description, which is given solely by way of example and with reference to the accompanying drawings, in which.

DETAILED DESCRIPTION OF THE INVENTION

Figure 1:
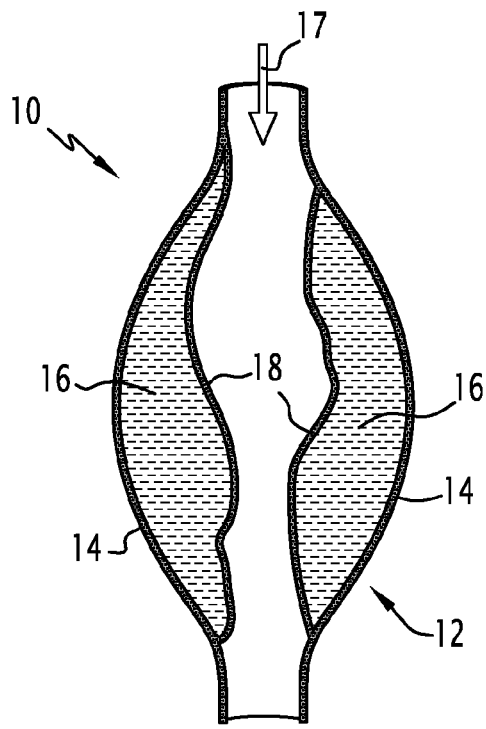
FIG. 1 is a cross-sectional view of an aneurysm.

Referring to FIG. 1, the aortic artery 10 of a patient has an aneurysm 12 resulting from a dilatation of part of a wall 14 forming the artery 10.

The aneurysm 12 as shown comprises a soft blood clot, or thrombus 16, which extends from the arterial wall 14 towards the centre of the aneurysm 12. The part of the thrombus 16 that is in contact with the circulating blood (represented by the arrow 17) often forms a membrane or intemna 18.

Figure 2:
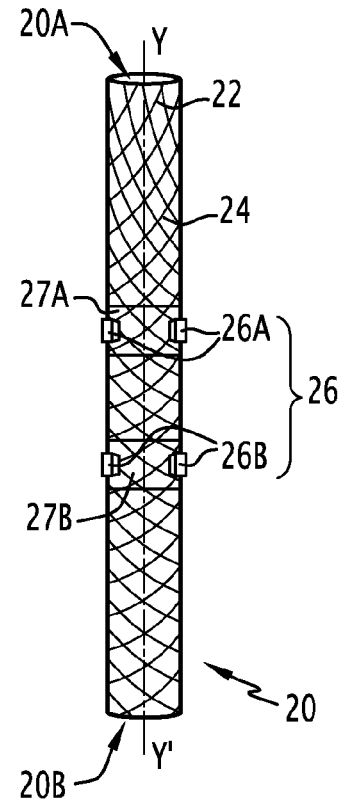
FIG. 2 is a front view of an endoprosthesis according to the invention equipped with pressure probes.

The endoprosthesis 20 shown in FIG. 2 is intended to exclude the aneurysm 12 from the circulating blood 17. The endoprosthesis 20 comprises a tubular mesh 22 embedded in an extensible fabric or film 24 which is blood-tight and biocompatible, such as an elastomer. The assembly constituted by the mesh 22 and the film 24 therefore forms a tubular envelope 22, 24 of the endoprosthesis 20. The mesh 22 is made of stainless steel or of an alloy having resilience properties, so that the endoprosthesis 20 is auto-extensible. Such an endoprosthesis is commonly known by the English term "stent".

The endoprosthesis 20 is capable of deforming spontaneously from a compressed state, in the present case having a small diameter, to a dilated state in which it has a larger diameter, the dilated state constituting its rest state. Owing to its resilience, the endoprosthesis 20, once fitted, is to press against the inside surface of the artery 10 on each side of the aneurysm 12, thus constituting an inner sleeve.

Before being fitted, the endoprosthesis 20 extends along a direction Y-Y'. In the example shown, the endoprosthesis 20 is "simple", that is to say it forms only a single straight tube. In other embodiments, according to the location of the aneurysm 12 along the artery 10, the endoprosthesis may be "double or bifurcate", that is to say it delimits on one side a single tube which divides to form, on the other side, two tubes. In this case, it is clear that the endoprosthesis 20 will extend along several different directions, according to the tube in question.

The endoprosthesis 20 further comprises a plurality of probes 26 which are fixed to the envelope 20, 24 and oriented towards the outside thereof.

The probes 26 are distributed in two groups, 26A and 26B. The probes of each group 26A, 26B are fixed to the same section, 27A and 27B, respectively, of the endoprosthesis 20, around its direction Y-Y' on its outer periphery. Each group of probes has a defined position along the endoprosthesis 20. Their position is identified, for example, in relation to one of the ends 20A, 20B of the endoprosthesis 20, such as the upper end 20A through which the circulating blood 17 is to enter.

Figure 3:
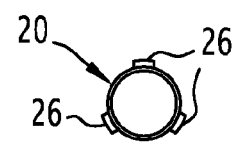
FIG. 3 is a diagram showing the elements of a probe fixed to the endoprosthesis.

As will be seen in FIG. 3, the probes 26 of each group are fixed around the endoprosthesis at equal intervals.

Figure 4:
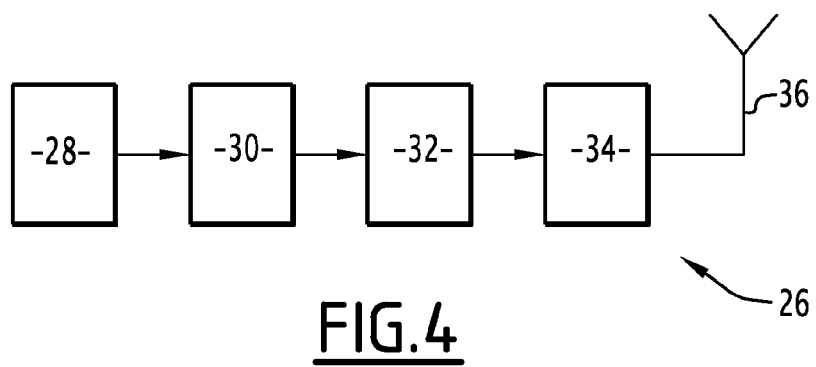
FIG. 4 is a cross-sectional view of a model of the aneurysm of FIG. 1.

Referring to FIG. 4, each probe 26 comprises a pressure sensor 28 which forms a transducer for delivering an analogue voltage as a function of the measured pressure. The sensor 28 measures the pressure locally, in the vicinity of a measurement surface (not shown). Nevertheless, the sensor 28 is capable of measuring the presence of endoleaks located at a distance from the measurement surface because the pressure generated by endoleaks leads to an overpressure in the region of the measurement surface.

The sensor 28 is directional, its sensitivity being maximal for pressures exerted perpendicularly to its measurement surface.

As will be explained hereinbelow, each probe 26 is fixed to the endoprosthesis 20 in such a manner that the sensor 28 is oriented perpendicularly to the envelope 22, 24, that is to say in such a manner that the measurement surface is parallel to the envelope 22, 24.

The voltage delivered by the sensor 28 is preferably of the differential type, in order to limit the measurement noise.

The sensor 28 measures an "absolute" pressure value, that is to say relative to a predetermined fixed reference (atmospheric pressure). The probes 26 thus differ from existing probes, which measure relative pressures taken at two different points within the aneurysm. Preferably, the measuring range of the sensor 28 extends from 10 to 300 mm of mercury.

The voltage delivered by the sensor 28 is introduced into a low noise amplifier 30 in order to shape the analogue signal. The low noise amplifier 30 comprises an instrumentation amplifier (not shown) having a common-mode rejection ratio of preferably greater than 80, and a low pass filter (also not shown) whose cut-off frequency is chosen so as to be able to retrieve the fundamental frequency of the signal but also sufficient harmonics to retrieve the systolic pressure. In fact, it has been found that a low rejection ratio leads to the presence of noise.

The cut-off frequency is determined taking account of the fact that the frequency of a patient has a value of from 0.3 to 2 Hz and choosing a safety factor of 5.

Each probe 26 then comprises an analogue/digital converter 32 for converting the analogue signal shaped by the low noise amplifier 30 into digital data. Preferably, the analogue/digital converter 32 has a resolution greater than 16 bits and a sampling frequency greater than 100 Hertz. It is in fact necessary, according to Shannon's theorem, to use a sampling frequency that is at least two times greater than 2 Hz (characteristic physiological frequency). Here, a safety factor of 50, that is to say 100 Hz, is taken. The architecture of the converter 32 is of the double-ramp type or preferably of the successive approximation type, because the latter is more rapid.

The digitized data are introduced into a transponder 34 which is to emit an electromagnetic signal by way of an antenna 36 which is to be positioned outside the patient's body.

The electronic architecture of each probe comprises all the elements (transducer, analogue/digital converter and transponder) which enable it to be regarded as a pressure probe of the RFID (Radio Frequency Identification) type.

The antenna 36 has a carrier frequency within one of the free frequency bands defined in the ISM (Industrial, Scientific and Medical) standard for the emission of data, which is specific to each probe 26. Accordingly, the signals emitted by each of the probes 26 can be differentiated from one another on the basis of the carrier frequencies used. It is thus very easy to select the signals emitted by a particular sensor. By way of variation, the signals can be differentiated on the basis of the sent digital data. This allows the manufacturing cost to be reduced, because only one software parameter has to be changed between probes, that is to say in the ISM bands (for example at 125 kHz, 13.56 MHz, 480 MHz, 900 MHz or 2.45 GHz), while in the preceding variant the very structure of the probes had to be modified. The two variants can be combined.

Figure 8:
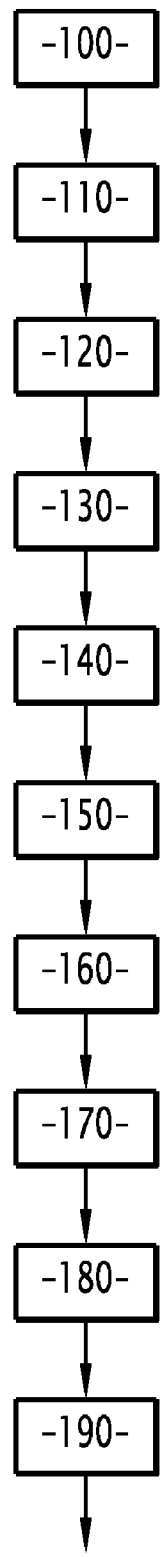
FIG. 8 is a block diagram of a method for producing the endoprosthesis.
Figure 9:
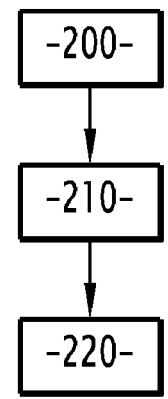
FIG. 9 is a block diagram of a method for using the implanted endoprosthesis.

Referring to FIG. 8, there will now be described a method for producing the endoprosthesis 20, especially how the groups of probes 26A and 26B are positioned along the endoprosthesis 20.

In a first step 100, a visual representation of the aneurysm 12 of the patient to be treated is obtained by medical imaging. This representation is preferably a view from a scanner or MRI, giving an image of the aneurysm similar, for example, to that of FIG. 1.

The choice between MRI and scanner is made especially according to the materials of which the endoprosthesis is made.

There follows a step 110 in which the envelope 22, 24, the shape of which is adapted to that of the aneurysm 12, is produced.

In a step 120, a model of the aneurysm is derived from the visual representation. A possible model is shown, for example, in FIG. 5. Simple shapes are used to correspond to the general shape of the actual aneurysm. In addition, a general direction of flow X-X' of the blood flow 17 is also determined in this step 120. This direction of flow X-X' preferably corresponds to the path which the blood would follow if there was no aneurysm. In the example described, this direction is straight, but it could be curved or even divide in the case of an aneurysm in the region of a branch.

The model is preferably produced with non-linear elasticity. During modelling, the various tissues are represented by a series of resilient media of different mechanical coefficients. For example, a different elastic coefficient will be chosen for the arterial wall of the aneurysm 14, for the thrombus 16, for the intemna 18 and for the blood 17 circulating in the artery 10.

The choice of different mechanical coefficients is made, in one embodiment, on the basis of the treatment of preceding patients, as will be explained hereinbelow.

The production method continues with a step 130 in which an echograph is produced, then with a step 140 in which the blood flow 17 at the entry to the aneurysm 12 is measured, on the basis of the echograph.

By virtue of the modelling of the tissues and the measurement of the blood flow, the fluid mechanics equations relating to the blood flow in the aneurysm are established and resolved in a step 150.

Owing to this resolution it is possible to obtain, in a step 160, the local pressure maxima exerted on the arterial wall 14 of the aneurysm 12. These are the most fragile locations where the risk of rupture is greatest.

In the embodiment described, the step 160 of locating the local maxima consists in determining the position, along the direction of flow X-X', of an at-risk portion of aneurysm perpendicular to the direction X-X'. In fact, the inventors have found that the weakened zones of the arterial wall 14 depend on the spatial geometry thereof and are generally concentrated in rings around the direction of flow X-X'. This is especially due to the fact that endoleaks generate an overpressure not only in the location at which they occur but also, to a lesser extent, all around the direction of flow X-X'.

Several at-risk portions are thus obtained, each corresponding to a weakened zone of the aneurysm 12. In the example shown, two portions have been determined, referenced A and B. Preferably, the height of those portions corresponds substantially to the size of each probe 26 along the endoprosthesis, when the probe is fixed.

Figures 5, 6:
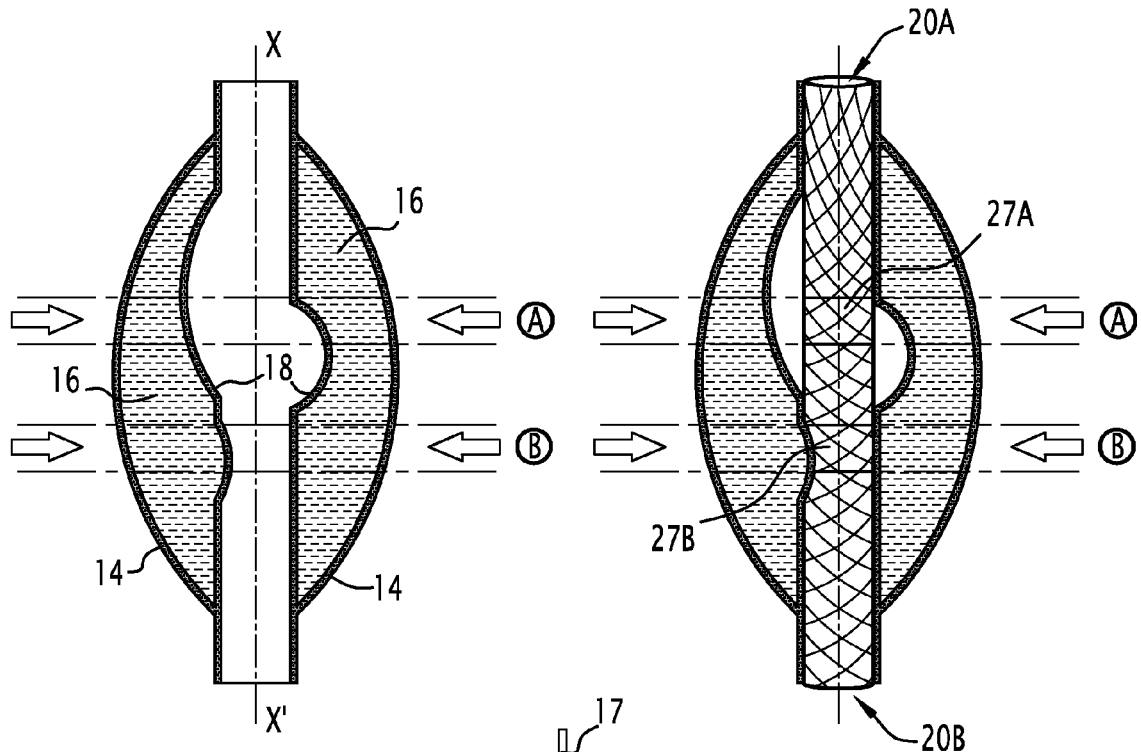
FIG. 5 is a view similar to that of FIG. 4, with the modelled endoprosthesis.
FIG. 6 is a top view of the endoprosthesis of FIG. 2.

Referring to FIG. 6, in a step 170 the direction Y-Y' of the endoprosthesis 20 is made to correspond with the direction of flow X-X', and then a configuration for fitting of the endoprosthesis 20, that is to say especially its position along the direction of flow X-X', is chosen on the model of the aneurysm 12.

In a step 180, the position of the fixing sections 27A, 27B for the groups of probes 26A, 26B are derived therefrom, the fixing sections corresponding to the intersection of the at-risk portions A, B with the envelope 22, 24 of the endoprosthesis 20.

Each section 27A, 27B is located along the endoprosthesis by its distance, along the direction Y-Y' of the endoprosthesis 20, in relation to one of the ends of the endoprosthesis 20, for example the upper end 20A.

The method then comprises a step 190 in which a plurality of probes is fixed to each section 17A, 27B, each plurality of probes fixed to the same section forming a group of probes 26A, 26B. The probes 26A, 26B of the same group are fixed around the direction of the endoprosthesis 20, at regular intervals. Each probe 26 is oriented perpendicularly to the envelope of the endoprosthesis 20, that is to say perpendicularly to the direction Y-Y'. Accordingly, the pressure can be measured in all the directions transverse to the direction Y-Y', in the at-risk portion in question of the aneurysm.

Preferably, the probes are fixed to the envelope of the endoprosthesis by adhesive bonding. The adhesive used will be of the biological type. This type of fixing makes it possible to avoid weakening the biocompatible fabric 24, as is the case, for example, when the probe is sewn onto the envelope.

Figure 7:
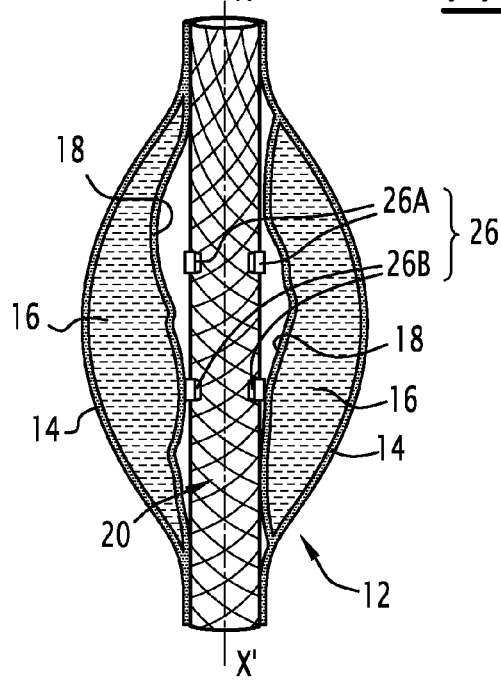
FIG. 7 is a view similar to that of FIG. 1, with the endoprosthesis fitted in the aneurysm.

The endoprosthesis 20 equipped with the probes 26A and 26B is implanted by conventional methods in order to arrange it in its fitting configuration chosen on the model. The fitted endoprosthesis is shown in FIG. 7.

It will be noted that, by virtue of the invention, the efficiency of the endoprosthesis once fitted is not sensitive to the angular orientation of the endoprosthesis around the direction of flow X-X' because the probes 26 are distributed equally around that direction. This considerably facilitates the fitting of the endoprosthesis, which can have any angular orientation.

A method for using the fitted endoprosthesis 20 will now be described.

Following fitting of the endoprosthesis 20, a monitoring device (not shown) situated outside the patient's body interrogates each of the probes 26 in a step 200 in order to determine the pressure in the aneurysm at the various points corresponding to the position of the probes 26.

On the basis of these actual pressure values, in a step 210, the model of the aneurysm is updated by modifying the coefficients of elasticity so that the updated model allows the pressure values actually obtained to be found. This is an inverse-type approach, in which the data supplied by the probes are compared with those obtained from the digital model of the same flow. Preferably, this updating is obtained by varying the physical parameters by a method for finding extrema by the so-called "retropropagation" technique.

This step 210 also supplies values of mechanical coefficients which may be used for subsequent patients (see step 110).

Once the coefficients have been updated, the pressure measurements of each of the sensors are taken at intervals determined by the operator. These readings are represented by the block 220.

Each measurement reading first makes it possible to determine if a local pressure associated with a probe 26 has increased suddenly, in which case there is a risk of rupture at the arterial wall 14 located along the orientation of the sensor, and more generally in the corresponding at-risk portion as a whole.

In addition, the digital model is used to determine the development of the pressure in the aneurysm 12 outside the zones covered by the probes 26 in order to detect the appearance of new weak zones outside the at-risk portions monitored by the sensors 26.

It will be noted that the prosthesis according to the invention can also be used in the case of an aneurysm resulting from a retraction of the vessel wall. In this case, the endoprosthesis serves to move the walls apart. The probes 26 are then adhesively bonded to the envelope 22, 24 while being oriented inwards. The pressure measurements make it possible to calculate the blood flow in order to ensure that the latter does not diminish, which would mean that the artery is obstructed again.

The invention claimed is:

1. A method for producing an endoprosthesis for implantation in a deformed region of a vessel of a patient, comprising:
   producing a tubular envelope which extends according to a direction, and
   fixing a plurality of pressure probes to the envelope, wherein each probe comprises:
   a sensor for carrying out a pressure measurement, and
   a transponder configured to emit an electromagnetic signal by way of an antenna, for transmitting only the pressure measurement obtained from the sensor of the probe to a monitoring device located outside the patient's body,
   wherein the transponder is suitable for generating an electromagnetic pressure measurement transmission signal containing at least one characteristic that is distinctive to the probe of which the transponder forms part and wherein the sensor of each pressure probe of the plurality of pressure probes is a directional sensor with a sensitivity being maximal for pressures exerted perpendicularly to the sensor's measuring surface,
   the method further comprising:
   obtaining a visual representation of the deformed region of the vessel of the patient by medical imaging,
   producing an envelope of a shape adapted to that of the deformed region of the vessel of the patient, locating at least one local pressure maximum exerted on the wall of the deformed region of the vessel of the patient by blood flows within the deformed region of the vessel, and fixing at least one of the pressure probes onto the envelope, the probe being oriented towards the outside of the envelope so that the probe is oriented towards the local pressure maximum when the endoprosthesis is implanted in the deformed region of the vessel.

2. The method according to claim 1, further comprising:
deriving a model of the deformed region of the vessel of the patient from the visual representation, and
locating by calculation the local pressure maximum or maxima exerted on the wall of the modelled deformed region of the vessel of the patient.

3. The method according to claim 2, wherein the visual representation is a view from a scanner or MRI.

4. The method according to claim 2, wherein fixing the pressure probe to the endoprosthesis comprises:
choosing a configuration for fitting of the endoprosthesis from the model of the deformed region of the vessel of the patient, such that the endoprosthesis extends along a direction of flow of the blood flow,
determining a zone for the fixing of sensors to the envelope of the endoprosthesis, such that the local maximum is located perpendicularly to the fixing zone relative to the envelope, and
fixing the pressure probe to the fixing zone, the probe being oriented perpendicularly to the envelope towards the outside of the endoprosthesis.

5. The method according to claim 4, further comprising:
determining an at-risk portion of the deformed region of the vessel of the patient, perpendicular to the direction of flow and forming the local maximum,
determining along the direction of the envelope in the configuration for fitting of the endoprosthesis, a section of the envelope delimited by the at-risk portion (A, B), the section forming the zone for fixing of the pressure probe.

6. The method according to claim 5, wherein the at-risk portion has a thickness corresponding to a dimension exhibited by the pressure probe along the direction of the envelope when the probe is fixed.

7. The method according to claim 6, further comprising:
fixing a plurality of probes to the fixing section around the direction of the endoprosthesis.

8. The method according to claim 7, wherein the probes are distributed around the direction of the envelope at regular intervals.

9. The method according to claim 1, wherein the deformed region of the vessel of the patient is an aneurysm.

* * * * *